US009763647B2

(12) United States Patent
Lee

(10) Patent No.: US 9,763,647 B2
(45) Date of Patent: *Sep. 19, 2017

(54) TRANSMIT/RECEIVE ISOLATION FOR AN ULTRASOUND SYSTEM

(71) Applicant: SAMSUNG MEDISON CO., LTD., Hongcheon-Gun, Gangwon-Do (KR)

(72) Inventor: Hong Gyo Lee, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/188,538

(22) Filed: Jun. 21, 2016

(65) Prior Publication Data

US 2016/0296209 A1 Oct. 13, 2016

Related U.S. Application Data

(63) Continuation of application No. 12/698,889, filed on Feb. 2, 2010, now Pat. No. 9,380,993.

(30) Foreign Application Priority Data

Mar. 5, 2009 (KR) .................. 10-2009-0018940

(51) Int. Cl.
A61B 8/00 (2006.01)
A61B 8/08 (2006.01)

(52) U.S. Cl.
CPC .............. *A61B 8/54* (2013.01); *A61B 8/00* (2013.01); *A61B 8/4444* (2013.01);
(Continued)

(58) Field of Classification Search
USPC ........................................ 600/437
See application file for complete search history.

(56) References Cited

U.S. PATENT DOCUMENTS 4,424,715 A 1/1984 Hansen
5,603,324 A 2/1997 Oppelt et al.
(Continued)

FOREIGN PATENT DOCUMENTS

JP 2001-353145 A 12/2001
JP 2004-230069 A 8/2004
(Continued)

OTHER PUBLICATIONS

Non-Final Office Action Japanese Patent Application No. 2010-026848 dated Jan. 21, 2014 with partial English translation.
(Continued)

*Primary Examiner* — Tse Chen
*Assistant Examiner* — Jason Ip
(74) *Attorney, Agent, or Firm* — McDermott Will & Emery LLP

(57) ABSTRACT

A transmit/receive isolation for an ultrasound system to block a high voltage transmit signal from being propagated to a receiving unit during a transmission period of an ultrasound signal is disclosed. An ultrasound system includes a switching unit coupled to a transmitting unit, a ultrasound probe and a receiving unit. The switching unit includes diode bridges and a switching module having pairs of switches connected to the respective diode bridges, wherein each pair of switches is configured to perform switching between a plus voltage and a minus voltage to forward-bias a corresponding diode bridge to allow a respective receive signal to be propagated to the receiving unit in a first state and to reverse-bias the corresponding diode bridge to block a respective transmit signal to be propagated to the receiving unit in a second state.

19 Claims, 3 Drawing Sheets

(52) U.S. Cl.
CPC ............ *A61B 8/4483* (2013.01); *A61B 8/461* (2013.01); *A61B 8/485* (2013.01); *A61B 8/488* (2013.01); *A61B 8/5207* (2013.01)

(56) References Cited

U.S. PATENT DOCUMENTS

| | | | |
|---|---|---|---|
| 5,768,939 | A | 6/1998 | Quayle et al. |
| 6,083,164 | A | 7/2000 | Oppelt et al. |
| 6,269,052 | B1 | 7/2001 | Oppelt |
| 6,511,432 | B2 | 1/2003 | Moore et al. |
| 6,937,176 | B2 | 8/2005 | Freeman et al. |
| 7,314,445 | B2 | 1/2008 | Wodnicki et al. |
| 2003/0115963 | A1 | 6/2003 | Song et al. |
| 2005/0068221 | A1 | 3/2005 | Freeman et al. |
| 2006/0061231 | A1 | 3/2006 | Kameishi |
| 2006/0115091 | A1 | 6/2006 | Kim et al. |
| 2009/0002073 | A1 | 1/2009 | Kim et al. |
| 2010/0014332 | A1 | 1/2010 | Shuey |

FOREIGN PATENT DOCUMENTS

| | | |
|---|---|---|
| JP | 2006-68090 A | 3/2006 |
| JP | 2006-87602 | 4/2006 |
| JP | 2006-101997 A | 4/2006 |
| JP | 2007-001463 A | 1/2007 |
| JP | 2007-319286 A | 12/2007 |
| JP | 2010-29255 A | 2/2010 |
| JP | 2010-148644 A | 7/2010 |
| KR | 10-2003-0055430 A | 7/2003 |
| KR | 10-2006-0059147 A | 6/2006 |
| KR | 10-2009-0000934 A | 1/2009 |
| WO | 00/61008 A1 | 10/2000 |
| WO | 03/096883 A2 | 11/2003 |
| WO | 2006/030355 A1 | 3/2006 |

OTHER PUBLICATIONS

Japanese Notice of Allowance issued in Japanese Application No. 2010-026848 dated Jul. 22, 2014, w/English translation.
Korean Office Action issued in Korean Patent Application No. KR 10-2009-0018940 dated Apr. 20, 2011.
U.S. Office Action issued in U.S. Appl. No. 12/698,889 dated Aug. 30, 2012.
U.S. Office Action issued in U.S. Appl. No. 12/698,889 dated Jan. 17, 2013.
U.S. Office Action issued in U.S. Appl. No. 12/698,889 dated Jun. 26, 2013.
U.S. Office Action issued in U.S. Appl. No. 12/698,889 dated Jul. 11, 2014.
U.S. Office Action issued in U.S. Appl. No. 12/698,889 dated Dec. 2, 2014.
U.S. Office Action issued in U.S. Appl. No. 12/698,889 dated Jun. 26, 2015.
Notice of Allowance issued in U.S. Appl. No. 12/698,889 dated Jun. 2, 2016.
European Search Report for Application No. 10151379.4-2319, mailed Mar. 22, 2010, 7 pages.

TRANSMIT/RECEIVE ISOLATION FOR AN ULTRASOUND SYSTEM

CROSS-REFERENCE TO RELATED APPLICATIONS

The application is a Continuation of U.S. patent application Ser. No. 12/698,889, filed on Feb. 2, 2010, which claims priority to Korean Patent Application No. 10-2009-18940, filed on Mar. 5, 2009, the disclosures of each are hereby incorporated by reference.

TECHNICAL FIELD

The present disclosure relates to ultrasound systems, and more particularly to transmit/receive isolation for an ultrasound system, with which a high voltage transmit signal is blocked from being propagated to a receiving unit during a transmission period.

BACKGROUND

Due to its non-invasive and non-destructive nature, an ultrasound system has been extensively used for acquiring internal information of a target object in the medical profession, Since the ultrasound system may provide a high resolution image to a doctor without a surgical treatment, which is performed by directly incising and observing the target object, it is very helpful in the medical profession.

Generally, an ultrasound system includes a transmit/receive switch. The transmit/receive switch connects a transmitting unit with an ultrasound probe during a transmission period of an ultrasound signal to transmit a high voltage transmit signal from a receiving unit to an ultrasound probe. At the same time, the transmit/receive switch blocks a transmit signal to be propagated to the receiving unit. The transmit/receive switch connects the receiving unit with the ultrasound probe during a receiving period of an ultrasound signal to transmit the receive signal outputted from the ultrasound probe, which receives the ultrasound. signal reflected from a target object (i.e. ultrasound echo signal), to the receiving unit.

When an ultrasound image in thin depth is obtained with the conventional ultrasound system, a high voltage transmit signal is propagated to the receiving unit. This is because the transmit/receive switch cannot completely block the transmit signal to be propagated to the receiving unit. This not only affects the receiving unit but also reduces quality of the ultrasound image.

SUMMARY

Embodiments of an ultrasound system for blocking a high voltage transmit signal to be propagated to a receiving unit during a transmission period of an ultrasound signal are disclosed herein.

In one embodiment, by way of non-limiting example, an ultrasound system comprises: a transmitting unit configured to form a plurality of transmit signals; an ultrasound probe configured to convert the transmit signals to a plurality of ultrasound signals, transmit the ultrasound signals to a target object, receive a plurality of echo signals reflected from the target object and form a plurality of receive signals based on the echo signals; a receiving unit; and a switching unit coupled to the transmitting unit, the ultrasound probe and the receiving unit and comprising a plurality of diode bridges each being switchable between first and second states such that the respective transmit signal is blocked from being propagated to the receiving unit when the diode bridge is in the first state and the respective receive signal is allowed to be propagated to the receiving unit when the diode bridge is in the second state.

In one embodiment, by way of non-limiting example, an ultrasound system comprises: a transmitting unit configured to form a plurality of transmit signals; an ultrasound probe configured to convert the transmit signals to a plurality of ultrasound signals, transmit the ultrasound signals to a target object, receive a plurality of echo signals reflected from the target object and form a plurality of receive signals based on the echo signals; a receiving unit; a switching unit coupled to the transmitting unit, the ultrasound probe and the receiving unit; a voltage measuring unit configured to measure a voltage of each of the transmit signals to form a measured voltage; and a control unit configured to perform the following steps: comparing the measured voltage with a predetermined threshold voltage, controlling the switching unit to block the transmit signal from being propagated to the receiving unit if the measured voltage is over the predetermined threshold voltage and controlling the switching unit to allow the receive signal to be propagated to the receiving unit if the measured voltage is below the predetermined threshold voltage.

In one embodiment, by way of non-limiting example, an ultrasound system comprises: a transmitting unit configured to form a plurality of transmit signals; an ultrasound probe configured to convert the transmit signals to a plurality of ultrasound signals, transmit the ultrasound signals to a target object, receive a plurality of echo signals reflected from the target object and form a plurality of receive signals based on the echo signals; a receiving unit; a switching unit coupled to the transmitting unit, the ultrasound probe and the receiving unit; a voltage measuring unit configured to measure a voltage of each of the transmit signals to form a measured voltage; and a control unit responsive to a blocking instruction to control the switching unit to block the corresponding transmit signal from being propagated to the receiving unit and further responsive to a non-blocking instruction to control the switching unit to allow the corresponding receive signal to be propagated to the receiving unit.

In one embodiment, by way of non-limiting example, an ultrasound system comprises: a transmitting unit configured to form a transmit signal; an ultrasound probe configured to convert the transmit signal to an ultrasound signal, the ultrasound probe being further configured to transmit the ultrasound signal to a target object during a transmit period, receive an echo signal reflected from the target object during a receive period and form a receive signal based on the echo signal; a receiving unit; and a switching unit coupled to the transmitting unit, the ultrasound probe and the receiving unit and comprising a plurality of diode bridges, each being configured to block the respective transmit signal from being propagated to the receiving unit during the transmit period and allow the respective receive signal to be propagated to the receiving unit during the receive period.

The Summary is provided to introduce a selection of concepts in a simplified form that are further described below in the Detailed Description. This Summary s not intended to identify key or essential features of the claimed subject matter, nor is it intended to be used in determining the scope of the claimed subject matter.

DETAILED DESCRIPTION

The present invention is described below in view of the provided drawings.

Figure 1:
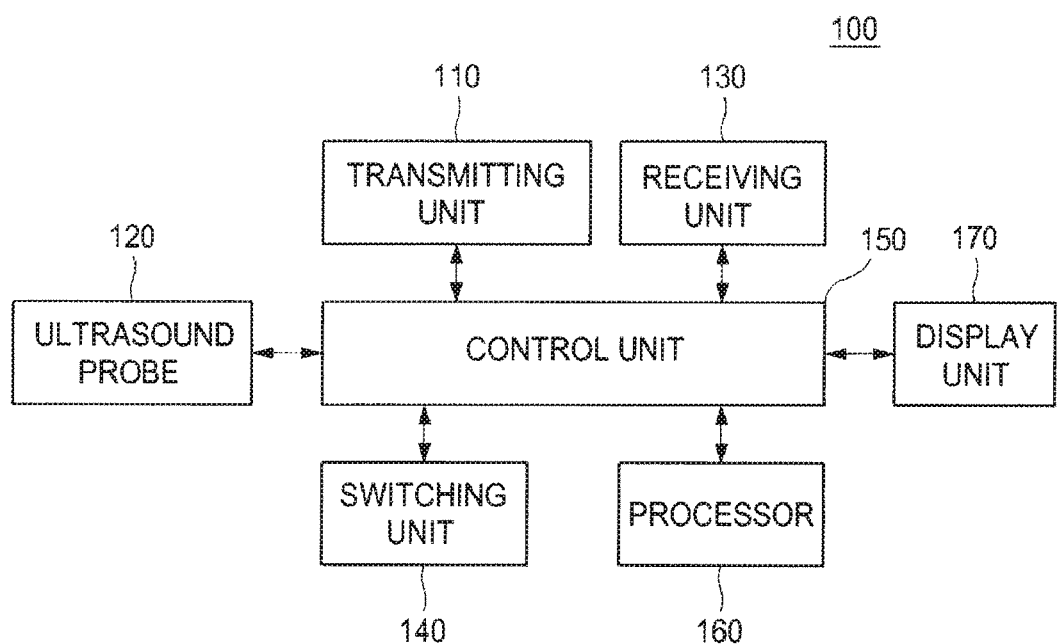
FIG. 1 is a block diagram showing an illustrative embodiment of an ultrasound system applied to a switching unit according to the present invention.

FIG. 1 is a block diagram showing an illustrative embodiment of an ultrasound system 100 applied to a switching unit 140 according to the present invention. A transmitting unit 110 forms a high voltage transmit signal to obtain frames. The frames include B mode (brightness mode) image, D mode (Doppler mode) image, c mode (color mode) image, elasticity image, etc.

An ultrasound probe 120 converts transmit signals to a plurality of ultrasound signals, transmits them to a target object, receives a plurality of echo signals reflected from the target object and forms a plurality of receive signals based on the ultrasound echo signals. The ultrasound probe 120 includes a plurality f transducer elements for converting an ultrasound signal into an electronic signal and vice-versa.

A receiving unit 130 converts a plurality of receive signals from the ultrasound probe 120 to analog signals. In addition, the receiving unit 130 focuses a plurality of receive signals, which are converted in digital, based on a focusing point and position of a transducer element on the ultrasound probe 120. The receiving unit 130 forms a plurality of ultrasound data by using the plurality of receive and focusing signals.

A switching unit 140 is coupled to the transmitting unit 110, the ultrasound probe 120 and the receiving unit 130. The switching unit 140 connects the transmitting unit 110 to the ultrasound probe 120 during a transmission period of an ultrasound signal and transmits a high voltage transmit signal from the transmitting unit 110 to the ultrasound probe 120. At the same time, the switching unit 140 blocks the transmit signal to be propagated to the receiving unit 130. Also, the switch unit 140 connects the receiving unit 130 with the ultrasound probe 120 during a receiving period of an ultrasound signal and transmits the receive signal from the ultrasound probe 120 to the receiving unit 130.

Figure 2:
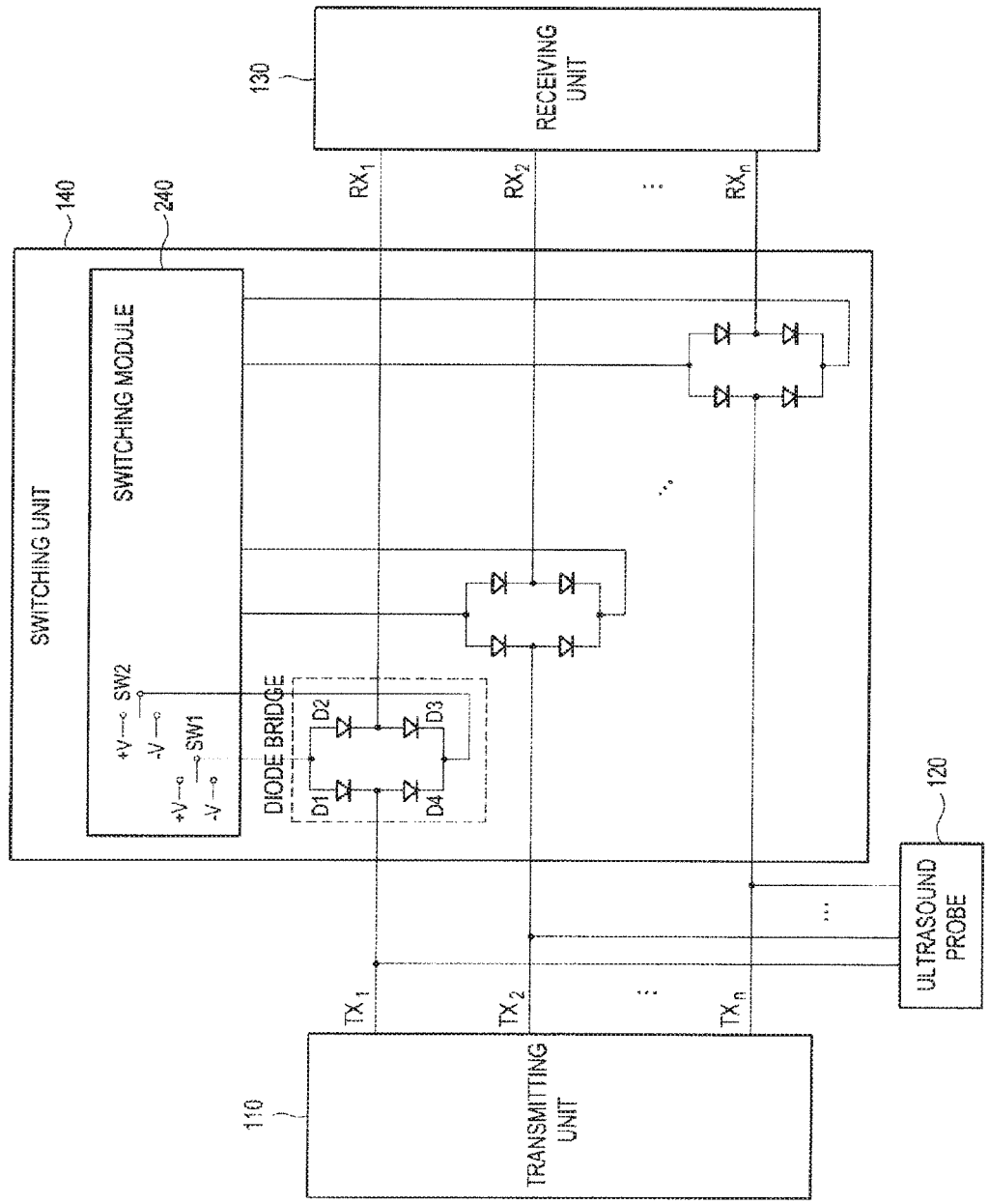
FIGS. 2 and 3 are is illustrative diagrams of switching units according to various embodiments of the present invention.
Figure 3:
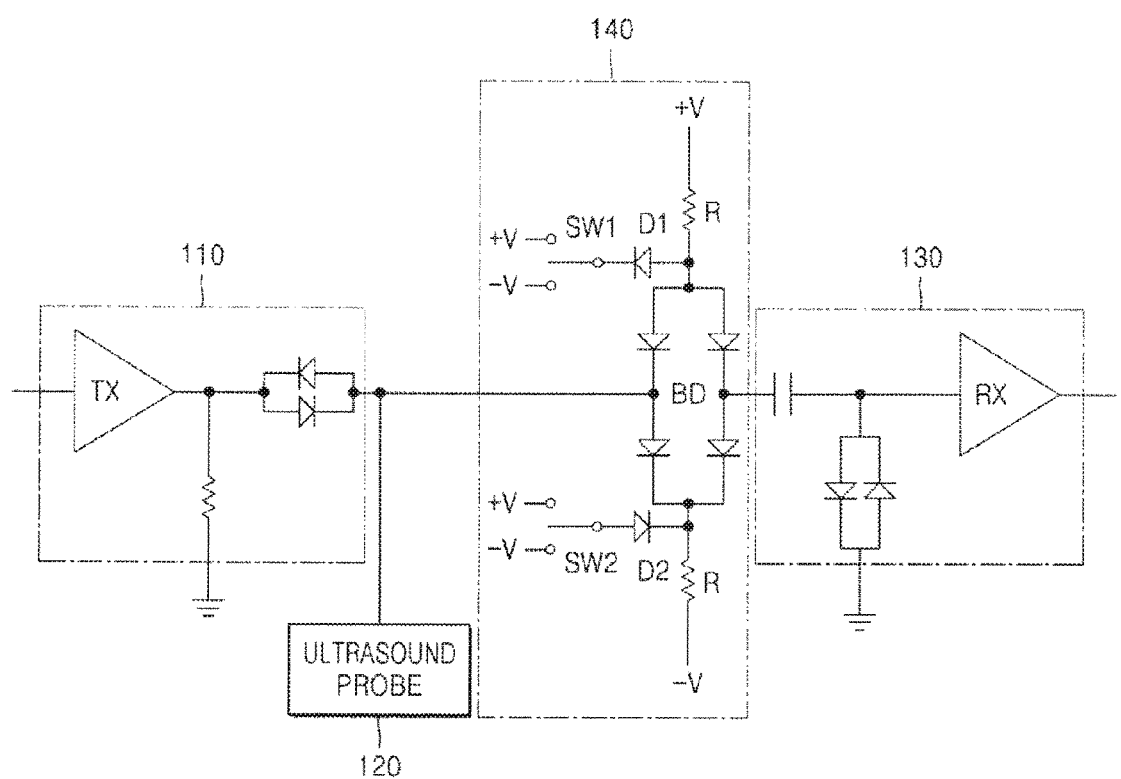

Now referring to FIGS. 2 and 3, the switching unit 140 is described for isolating the receiving unit 130 from transmit signal transmitted from the transmitting unit 110 during the transmission period of the ultrasound signal. In one embodiment, the switching unit 140 comprises a plurality of diode bridges as shown in FIG. 2, one of which is shown in detail in FIG. 3. Each diode bridge is switchable between first and second states such that the respective transmit signal is blocked from being propagated to the receiving unit 130 when the diode bridge is in the first state and the respective receive signal is allowed to be propagated to the receiving unit 130 when the diode bridge is in the second state. The switching unit 140 further comprises a switching module 240 connected to the diode bridges. The switching module 240 is operable to reverse-bias the diode bridge in the first state and forward-bias the diode bridge in the second state. In one embodiment, the switching module 240 comprises a pair of switches. During the transmission period of an ultrasound signal, a first switch SW1 is connected to a minus voltage terminal −V and a second switch SW2 is connected to a plus voltage terminal +V, to make the diode bridge off. Thus, a high voltage signal from the transmitting unit 110 may not be propagated to the receiving unit 130 and the receiving unit 130 can be completely isolated. On the other hand, during the receiving period of an ultrasound signal, the first switch SW1 is connected to the plus voltage terminal +V and the second switch SW2 is connected to a minus voltage terminal −V. Thus, the diode bridge is on and forward bias current may be propagated to the diode bridge. As such, the receive signal from the ultrasound probe 120 is transmitted to the receiving unit 130 via the diode bridge. The first and second switches can be implemented with mechanical relay transistors, field effect transistors (FET), etc. The switching module 240 is configured to control the diode bridges to be individually or simultaneously switchable.

Now referring FIG. 1, the control unit 150 controls the switching unit 140. Also, the control unit 150 controls transmit/receive of an ultrasound signal, as well as the formation and display of ultrasound images. The control unit 150 is responsive to a blocking instruction to control the switching unit to block the corresponding transmit signal from being propagated the receiving unit, the control unit is further responsive to a non-blocking instruction to control the switching unit to allow the corresponding receive signal to be propagated to the receiving unit.

A processor 160 forms ultrasound images by using a plurality of ultrasound data from the receiving unit 130. A display unit 170 displays ultrasound images formed in the processor 160.

In one embodiment, an ultrasound system may include a voltage measuring unit. The voltage measuring unit may measure voltage of each of transmit signals during a transmission period of ultrasound signals and form a measured voltage. The control unit 150 may be operable to perform the following steps: comparing the measured voltage with a predetermined threshold voltage, controlling the switching unit 140 to block the respective transmit signal from being propagated to the receiving unit 130 if the measured voltage is over the predetermined threshold voltage, controlling the switching unit 140 to allow the respective receive signal to be propagated to the receiving unit 130 if the measured voltage is below the threshold voltage.

Although embodiments have been described with reference to a number of illustrative embodiments thereof, it should be understood that numerous other modifications and embodiments can be devised by those skilled in the art fall within the spirit and scope of the principles of this disclosure. More particularly, numerous variations and modifications are possible in the component parts and/or arrangements within the scope of the disclosure, the drawings and the appended claims. In addition to variations and modifications in the component parts and/or arrangements, alternative uses will so be apparent to those skilled in the art.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The invention claimed is:

1. An ultrasound system, comprising:
a transmitting unit configured to form a transmit signal;
an ultrasound probe comprising a plurality of transducer elements and configured to receive the transmit signal from the transmitting unit, convert the transmit signal into an ultrasound signal, transmit the ultrasound signal to a target object, receive a respective echo signal from the target object in each of the plurality of transducer elements, and form a respective receive signal based on the respective echo signal in each of the plurality of transducer elements;

receiving unit comprising a plurality of inputs each associated with a respective transducer element of the plurality of transducer elements and each configured to receive the respective receive signal from the respective transducer element of the plurality of transducer elements of the ultrasound probe;

a plurality of diode bridges each coupled to a respective output of the transmitting unit and a respective transducer element of the ultrasound probe at one end of the diode bridge and coupled to a respective input of the plurality of inputs of the receiving unit at another end of the diode bridge and configured to operate in a first state in which a signal from the one end is blocked from being propagated to the other end or in a second state in which the signal from the one end is allowed to be propagated to the other end; and a control unit configured to:

control the plurality of diode bridges to be operated in the first state to block the transmit signal from the transmitting unit from being propagated to the receiving unit when the ultrasound probe is in a transmission period in which the ultrasound signal is transmitted from the ultrasound probe to the target object; and control the plurality of diode bridges to be operated in the second state to allow the receive signal from the probe to be propagated to the receiving unit when the ultrasound probe is in a receiving period in which the echo signal is received by the ultrasound probe from the target object, wherein the control unit controls the diode bridges of the plurality of diode bridges to be individually switchable, and wherein the control unit comprises, for each respective diode bridge, first and second switches configured to control the respective diode bridge to be operated in the first state or the second state, wherein the first switch is connected to one terminal of the respective diode bridge and the second switch is connected to another terminal of the respective diode bridge.

2. The ultrasound system of claim 1,
wherein the respective diode bridge is off in the first state, and the respective diode bridge is on in the second state.

3. The ultrasound system of claim 2,
wherein the first and second switches control to reverse-bias the respective diode bridge in the first state and forward-bias the respective diode bridge in the second state.

4. The ultrasound system of claim 1,
wherein the first switch performs switching between a first voltage and a second voltage different from the first voltage and the second switch performs switching between a third voltage and a forth voltage different from the third voltage.

5. The ultrasound system of claim 1,
wherein the control unit controls each diode bride to be operated in the first state by connecting the first switch to a plus voltage and the second switch to a minus voltage, and controls the diode bridge to be operated in the second state by connecting the first switch to the minus voltage and the second switch to the plus voltage.

6. The ultrasound system of claim 1, further comprising a voltage measuring unit configured to measure a voltage of the transmit signal,
wherein the control unit determines whether the ultrasound probe is in the transmission period or in the receiving period by comparing the voltage of the transmit signal with a predetermined threshold voltage.

7. The ultrasound system of claim 6, wherein the control unit determines the ultrasound probe is in the transmission period when the voltage of the transmit signal is higher than the predetermined threshold voltage, and determines the ultrasound probe is in the receiving period when the voltage of the transmit signal is lower than the predetermined threshold voltage.

8. The ultrasound system of claim 1, wherein each diode bridge has four terminals, and a first terminal of each diode bridge is coupled to the respective output of the transmitting unit and the respective transducer element of the ultrasound probe, a second terminal of each diode bride is coupled to the respective input of the receiving unit, and third and fourth terminals of each diode bridge are coupled to the control unit.

9. The ultrasound system of claim 8, wherein each diode bridge includes two diodes coupled in series between the third terminal of the diode bridge coupled to the control unit and the fourth terminal of the diode bridge coupled to the control unit.

10. The ultrasound system of claim 9, wherein each diode bridge includes two diodes coupled in series between the first terminal of the diode bridge coupled to the transmitting unit and the ultrasound probe and the second terminal of the diode bride coupled to the receiving unit.

11. The ultrasound system of claim 8, wherein the control unit controls each diode bridge to be operated in the first state to block the transmit signal from being propagated from the first terminal to the second terminal by applying a first voltage across the third and fourth terminals of the diode bridge.

12. The ultrasound system of claim 11, wherein the control unit controls each diode bridge to be operated in the second state to allow the receive signal to be propagated from the first terminal to the second terminal by applying a second voltage different from the first voltage across the third and fourth terminals of the diode bridge.

13. The ultrasound system of claim 12, wherein the second voltage is of an opposite polarity to the first voltage.

14. The ultrasound system of claim 1, wherein each diode bridge has four terminals, and a first terminal of each diode bridge is coupled to the respective output of the transmitting unit and the respective transducer element of the ultrasound probe, a second terminal of each diode bride is coupled to the respective input of the receiving unit, a third terminal of each diode bridge is coupled to the first switch, and a fourth terminal of each diode bridge is coupled to the second switch.

15. The ultrasound system of claim 14, wherein each diode bridge includes two diodes coupled in series between the first terminal of the diode bridge coupled to the transmitting unit and the ultrasound probe and the second terminal of the diode bride coupled to the receiving unit.

16. The ultrasound system of claim 15, wherein each diode bridge includes two diodes coupled in series between the third terminal of the diode bridge coupled to the first switch and the fourth terminal of the diode bridge coupled to the second switch.

17. The ultrasound system of claim 1, wherein the first switch is connected to one terminal of the respective diode bridge through a first diode and second switch is connected to another terminal of the respective diode bridge through a second diode.

19. The ultrasound system of claim 17, wherein, for each respective diode bridge, an anode of the first diode is connected to anodes of two diodes of the respective diode bridge, a cathode of the first diode is connected to the first switch, a cathode of the second diode is connected to cathodes of two other diodes of the respective diode bridge, and an anode of the second diode is connected to the second switch.

19. Thu ultrasound system of claim 18, wherein, for each respective diode bridge, the anode of the first diode is further connected to the plus voltage via a resistor, and the cathode of the second diode is further connected to the minus voltage via another resistor.

* * * * *